United States Patent [19]

Hermolin

[11] Patent Number: 4,465,861
[45] Date of Patent: Aug. 14, 1984

[54] PROCESS FOR PRODUCING A MIXTURE CONTAINING CYCLOHEXANOL AND CYCLOHEXANONE

[75] Inventor: Joshua Hermolin, Wilmington, Del.

[73] Assignee: E. I. Du Pont de Nemours and Company, Wilmington, Del.

[21] Appl. No.: 483,666

[22] Filed: Apr. 11, 1983

[51] Int. Cl.$^3$ .............................................. C07C 45/53
[52] U.S. Cl. .................................... 568/342; 568/835
[58] Field of Search ................ 568/342, 835, 798, 385

[56] References Cited

U.S. PATENT DOCUMENTS

| | | |
|---|---|---|
| 2,609,395 | 9/1952 | Dougherty et al. ................. 260/586 |
| 2,675,407 | 4/1954 | Gallo et al. ........................... 260/533 |
| 2,851,496 | 9/1958 | Cates, Jr. et al. .................... 260/586 |
| 3,093,686 | 6/1963 | Simon et al. ......................... 260/586 |
| 3,530,185 | 9/1970 | Pugi ..................................... 260/586 |
| 3,917,708 | 11/1975 | Kuessner et al. .................... 260/586 |
| 3,923,895 | 12/1975 | Costantini et al. .................. 260/586 |
| 3,925,316 | 12/1975 | Brunie et al. ........................ 260/586 |
| 3,927,105 | 12/1975 | Brunie et al. ........................ 260/586 |
| 3,957,876 | 5/1976 | Rapoport et al. .................... 260/586 |
| 3,987,100 | 10/1976 | Barnette et al. ..................... 260/586 |
| 4,326,084 | 4/1982 | Druliner et al. ..................... 568/360 |
| 4,341,907 | 7/1982 | Zelonka .............................. 568/360 |

OTHER PUBLICATIONS

Semenchenko et al., Russ. J. Phys. Chem. 47, 654, (1973).
Hoch et al., J. Prakt. Chem., 9, 173, (1959).
Kamiya, Chem. Abstr. 72, 11793Y, (1970).
Ochiai, Tetrahedron 20, 1819, (1964).

Primary Examiner—James H. Reamer
Attorney, Agent, or Firm—Frederick D. Hunter

[57] ABSTRACT

There is disclosed an improved process of decomposing a reaction mixture containing cyclohexyl hydroperoxide to form a mixture containing cyclohexanone and cyclohexanol comprising using in the decomposition step a catalyst composition consisting essentially of (a) a specified salt of chromium, cobalt, iron, manganese, molybdenum or vanadium and (b) as a stabilizing agent, an alkylsulfonic acid, an alkylarenesulfonic acid, an alkylammonium sulfonate, or an alkylphosphonium sulfonate.

12 Claims, No Drawings

PROCESS FOR PRODUCING A MIXTURE CONTAINING CYCLOHEXANOL AND CYCLOHEXANONE

BACKGROUND OF THE INVENTION

This invention relates to an improved process for producing a mixture containing cyclohexanol and cyclohexanone. More particularly, the invention relates to an improvement in the catalytic process for production of a mixture containing cyclohexanol and cyclohexyl hydroperoxide wherein cyclohexane is oxidized in air to produce a reaction mixture containing cyclohexyl hydroperoxide (CHHP) and the cyclohexyl hydroperoxide is decomposed.

The principle products of the decomposition, cyclohexanone and cyclohexanol, are readily converted by oxidation to adipic acid. Adipic acid is used in large volume in the preparation of condensation polymers, particularly polyamides.

The oxidation of cyclohexane to mixtures containing cyclohexanones and cyclohexanol is a well-known, competitive, large-volume industrial process. The product is frequently referred to as K/A (Ketone-Alcohol) mixture. Experience in the operation of the process which is reflected in the disclosures of many patents, has taught that the oxidation must be carried out at low conversion, if it is desired to maximize the yield of K and A and to minimize the formation of other oxidation products, some of which have deleterious effects in the production of adipic acid and/or on the purity of the adipic acid produced. Relatively minor process improvements, such as in the yield of K and A, can result in highly beneficial cost advantage.

Patents directed to the oxidation of cyclohexane include U.S. Pat. Nos. 2,675,407; 3,093,686; 3,530,185; 3,917,708; 3,957,876; 3,987,100; and 4,341,907.

An important step in the rather complicated overall oxidation process is the decomposition of cyclohexyl hydroperoxide, which is a primary oxidation product of cyclohexane. Since the efficiency of this decomposition step contributes to the efficiency of the overall oxidation process, improvements in the decomposition of CHHP are a desirable objective.

A number of ways of decomposing CHHP have been described.

U.S. Pat. No. 2,609,395, issued to Dougherty et al. on Sept. 2, 1952, discloses a process for oxidation of cycloalkanes to produce cycloalkanols and cycloalkanones, wherein a cycloalkane is reacted with limited quantities of oxygen. The cycloalkane hydroperoxides thereby produced are decomposed by heating in the presence of a cycloalkane, producing cycloalkanols and cycloalkanones.

U.S. Pat. No. 2,851,496, issued on Sept. 9, 1958 to Cates, Jr., et al., discloses a process for oxidation of naphthenes, particularly cyclohexane, in the liquid phase using a gas containing molecular oxygen followed by destruction of the resulting hydroperoxide by including in the overall process, after from 1 to 12% or more of the naphthene molecules have been oxidized, a controlled decomposition of peroxides on a bed of solid catalyst in the absence of any reducing agent or oxygen. Suitable catalysts include solid metallic substances in the form of granules, preferably comprising an inert supported impregnated with a metal of group VIII or an oxide of a metal of group VIA.

U.S. Pat. No. 3,923,895, issued to Costantini et al. on Dec. 2, 1975, discloses a process for the preparation of a mixture of a cycloalkanone and cycloalkanol by oxidation of a cycloalkane in the liquid phase by means of a gas containing molecular oxygen, following by heating the resulting solution of cycloalkyl hydroperoxide in the corresponding cycloalkane, at 80°–150° C., in the presence of a soluble chromium derivative as a catalyst, wherein at least a part of the heating of the hydroperoxide solution is carried out in the presence of a monoester or diester of orthophosphoric acid which is soluble in the reaction medium. Suitable compounds include alkyl, cycloalkyl, aryl and aralkyl esters. The process is said to minimize the formation of insoluble product which reduces heat exchange across the walls of the apparatus being used by coating thereon.

U.S. Pat. No. 3,925,316, issued to Brunie et al. on Dec. 9, 1975, discloses a process for preparing a mixture of cycloalkanol and cycloalkanone, particularly cyclohexanol and cyclohexanone, consisting of heating a solution of a cycloalkyl hydroperoxide in the corresponding cycloalkane in the presence of a catalyst which is a soluble derivative of vanadium, molybdenum or ruthenium. Suitable soluble catalysts include naphthenates, octoates, stearates and carbonyl derivatives. The process is stated to solve several previous problems including deactivation of the catalyst due to the formation of viscous polycondensates, such as polyesters.

U.S. Pat. No. 3,927,105, issued to Brunie et al. on Dec. 16, 1975, discloses a process for the preparation of a mixture of cycloalkanol and cycloalkanone, particularly cyclohexanol and cyclohexanone, which is rich in the cycloalkanone comprising heating a solution of a cycloalkyl hydroperoxide in the corresponding cycloalkane at from 80° to 150° C. in the presence of a soluble chromium compound as a catalyst, in a series of separate reaction zones, each having the hydroperoxide concentration maintained at an essentially uniform value throughout the zone. Naphthenates, octoates and stearates are among suitable catalysts.

U.S. Pat. No. 3,987,100, issued to Barnette et al. on Oct. 19, 1976, discloses cyclohexane oxidation in the presence of a binary catalyst system comprising specific amounts of chromium and cobalt, reacting any cyclohexyl hydroperoxide that may be formed in the presence of said binary catalyst system, and recovering a product consisting of cyclohexanone and cyclohexanol in a specified ratio.

U.S. Pat. No. 4,326,084, issued to Druliner et al. on Apr. 20, 1982, discloses an improved process for oxidizing cyclohexane to produce a reaction mixture containing cyclohexyl hydroperoxide and decomposing the cyclohexyl hydroperoxide to form a mixture containing cyclohexanone and cyclohexanol comprising using in the oxidation step and/or the decomposition step, as a catalyst, a transition metal complex of certain 1,3-bis(-pyridylimino)isoindolines. Usable transition metals are cobalt, manganese and iron.

Semenchenko et al., *Russ. J. Phys. Chem.* 47 (5), 654, (1973) have found that the decomposition of CHHP in cyclohexane in the presence of cobalt stearate is initially rapid and then slows down, i.e., the activity of the catalyst falls rapidly as the hydroperoxide decomposes.

Certain cobalt complexes with anionic heterocyclic nitrogen-donor ligands apparently catalyze the decomposition of other organic hydroperoxides. For example, Hock and Kropf, *J. Prakt. Chem.* 9, 173, (1959) tested the phthalocyanine derivatives of seven different metals as catalysts for the autoxidation of cumene (isopropylbenzene). They found that cobalt phthalocyanine gave the highest overall conversion of cumene to oxidation products, the highest conversion of cumene to K/A mixture, and the lowest conversion to cumene hydroperoxide in the final product mixture. Since the ketone and alcohol (acetophenone and 2-phenyl-2-propanol) are known to be decomposition products of the hydroperoxide, it can be inferred that the cobalt compound was the best catalyst for the decomposition of the hydroperoxide. The amount of hydroperoxide in the final product mixture was small but significant, and corresponded to 5.8% of the cumene originally charged.

Kamiya, *Kogyo Kagaku Zasshi* 72 (8), 1693, (1969); *Chem. Abstr.* 72, 11793Y, (1970) reports that cobalt phthalocyanine was a better catalyst than cobalt dodecanoate in the oxidation of cumene, and for the autoxidation of ethylbenzene. In each case the activity was "due to the decomposition of hydroperoxides".

Ochiai, *Tetrahedron* 20, 1819, (1964) studied the mechanisms by which transition metal stearates and transition metal phthalocyanines, including those of cobalt, participate in the autoxidation of cyclohexene.

It is known that the use of cyclohexane-soluble $Cr^{+3}$ complexes to catalyze the decomposition of CHHP offers the possibility of obtaining high K and A yields, high K/A ratio, and low DCHP formation. In order to achieve the yield improvement, the CHHP decomposition should be run at a temperature range of about 110°-130° C. However, CHHP decomposition with $Cr^{+3}$ catalyst is also known to cause severe fouling and insufficient decomposition of CHHP and to be sensitive to adventitious impurities. A major cause of fouling is the presence of short chain carboxylic acids, such as acetic acid, which cause precipitation of chromium compounds. These acids can be removed by water washing the process stream; however, the water causes the formation of insoluble hydroxide complexes. A process which alleviates these problems is desirable.

SUMMARY OF THE INVENTION

The present invention provides an improvement in a process for producing a mixture containing cyclohexanol and cyclohexanone wherein cyclohexane is oxidized to provide a reaction mixture containing cyclohexyl hydroperoxide and the cyclohexyl hydroperoxide is subsequently decomposed in the presence of starting cyclohexane to provide a mixture containing cyclohexanol and cyclohexanone. The improvement comprising conducting the decomposition step by contacting a reaction mixture containing cyclohexane and from about 0.1 to about 10% by weight of cyclohexyl hydroperoxide with a catalytic amount of a catalyst composition consisting essentially of (a) at least one cyclohexane-soluble salt of transition metal selected from the group consisting of chromium, cobalt, iron, manganese, molybdenum and vanadium and having an anion selected from the group consisting of carboxylates, sulfonates, alkylphosphates and (b) a sulfonate anion of a cyclohexane-soluble compound selected from the group consisting of alkyl- and alkylarenesulfonic acids alkylammonium sulfonates, alkylphosphonium sulfonates, and mixtures thereof, at a temperature of from about 80° to 130° C., at a pressure of from 210–2410 kPa gauge, and at a mol ratio of sulfur to transition metal of from about 0.1 to about 100.

DETAILED DESCRIPTION OF THE INVENTION

In the process of the invention a stabilizing agent, a sulfonate anion in the form of an alkylsulfonic acid, alkylarenesulfonic acid, alkylammonium sulfonate, or alkylphosphonium sulfonate is included in the catalyst composition to keep the transition metal ions in solution, thereby eliminating fouling of the reactor and the associated pipelines for conducting the reaction mixture. By maintaining the transition metal ions in solution, the activity of the catalyst is also prolonged. Hence, the process of the invention provides increased CHHP decomposition activity and, when the transition metal is chromium, higher K/A ratios and lower amounts of dicyclohexyl peroxide (DCHP) formation.

The transition metal compounds used in the catalyst composition for the process of the invention are commercially available and are selected from cyclohexane-soluble salts of chromium, cobalt, iron, manganese, molybdenum or vanadium. The salt has an anion which is a carboxylate, sulfonate, alkylphosphate. Preferably, each alkyl group has from 8 to 22 atoms. Preferably, the transition metal is chromium or cobalt. Most preferably, the transition metal is chromium because salts of chromium provide higher conversion of CHHP to K and A. Suitable cyclohexane soluble carboxylates include naphthenates, octoates, laurates, palmitates, stearates, linoleates and acetylacetonates. Suitable sulfonates include octylsulfonates, dodecylsulfonates and laurylsulfonates. Suitable alkyl phosphates include monooctyl phosphate, monododecyl phosphate, monolauryl phosphate, dioctyl phosphate, didodecyl phosphate and dilauryl phosphate.

The other component of the catalyst composition used in the process of the present invention is a cyclohexane-soluble sulfonate or sulfonic acid selected from alkylsulfonic acid, alkylarenesulfonic acid, alkylammonium sulfonate, and alkylphosphonium sulfonate, which serves as a stabilizing agent. It is to be understood that the presence of the sulfonate anion is the stabilizing factor and that the cation is relatively unimportant so long as the sulfonate stays in solution. In either case (stabilizing agent or salt), preferably, the alkyl group has from 8–22, preferably from 8–12 carbon atoms. Preferred alkylarenesulfonic acids are dodecylbenzenesulfonic acid and dinonylnaphthalenesulfonic acid, since they are available commercially.

The two components of the catalyst composition used in the process of the invention are present in amounts such that the mol ratio of sulfur to transition metal is from about 0.1 to about 100; preferably from about 1 to about 10. The stabilizing agent can be added to the CHHP process stream, as it leaves the cyclohexane oxidizer, can be added simultaneously with addition of the transition metal compound to the CHHP process stream or can be added downstream in the CHHP reactor. Preferably, it is added approximately concurrent with the transition metal catalyst compound and added to the process stream before the decomposition stage. The process stream can be water-washed prior to addition of the catalyst composition.

In the process of the invention a reaction mixture containing cyclohexane and cyclohexyl hydroperoxide is contacted with the catalyst composition at a temperature from about 80° to about 130° C., preferably from about 110° to about 130° C. Temperatures significantly lower than 80° C. may lead to unacceptably slow decomposition rates. Temperatures greater than 130° C. can be used but lead to significant uncatalyzed thermal decomposition of CHHP and lower yields of K and A.

The reaction mixture can be the solution received from the first step of the cyclohexaneoxidation process or the solution obtained by removal of some of the constituents by known processes. The concentration of CHHP in the reaction mixture can be from about 0.1% to about 10% by weight and is preferably from about 0.5 to about 3% by weight based on the total reaction mixture. Preferably, the catalyst composition is present in an amount sufficient to provide from about 0.1 to about 100, most preferably from about 0.1 to about 10 ppm of metal by weight based on the total reaction mixture. The time will depend on the temperature and the catalyst concentration and will usually be from about 5 to about 60 minutes. Longer times can be used, but usually no advantage results.

Pressures of from about 210 to about 2410 kPa (30 to 350 psi) gauge can be employed. The process of the invention can be performed by a batch method or a continuous method, but it is preferred to operate it in a continuous mode.

The invention is further illustrated by the following examples in which all temperatures are in degrees Celsius and all percentages are by weight unless otherwise specified.

EXAMPLES

The apparatus used in Examples 1-9 was a stainless-steel pulse reactor having a volume of about 125 ml and usable at internal pressures up to about 300 psi (2070 kPa) gauge pressure. The apparatus had a pressure-relief valve to insure that allowable pressure was not exceeded and was equipped with a side-arm with a septum for injection of liquid from a hypodermic syringe. Liquid contents (usually about 25 ml) in the apparatus could be stirred by an external magnetic drive. Temperatures were measured with a platinum resistance thermometer using digital temperature display and analog output.

CHHP decomposition experiments were performed under conditions which simulate plant process conditions. The activity of the transition metal cation was determined by measuring the amount of CHHP decomposed using gas chromotographic (GC) analysis.

EXAMPLE 1-9

Solutions of CHHP in cyclohexane containing chromium octoate and dodecylbenzenesulfonic acid (Examples 1-8) or dinonylnaphthalenesulfonic acid (Example 9 and Control) as a catalyst composition were decomposed. The dinonylnaphthalenesulfonic acid used was a commercial product containing 50% active ingredient. Operating conditions and results are presented in Table 1. Four different plant solutions were used. Solutions 2-4 were plant streams (tails) resulting from air oxidation of cyclohexane whereas solution 1 was a similar stream which had been water washed. Examples 1 and 2 show that when the S/Cr ratio was changed from 0.5 to 2, the amount of CHHP remaining in the product decreased 42%. Example 3 shows that there is an optimum for the amount of stabilizing agent needed since the CHHP remaining in the product is greater than that in Example 2. The optimum value for the stabilizing agent will depend upon such factors as the agent itself, the content of the CHHP reaction mixture and the transition metal salt being used. Example 9 and the Control experiment show that when chromium is the catalytic metal the amount of CHHP remaining in the product is 37% greater with unstabilized catalyst as compared to the stabilized catalyst composition of the invention.

TABLE 1

| Ex. | Solution | ppm $Cr^{+3}$ | Temp. | S/Cr | % Product A | K | CHHP | DCHP |
|---|---|---|---|---|---|---|---|---|
|  | 1 |  |  |  | 0.87 | 0.51 | 0.75 | 0.016 |
|  | 2 |  |  |  | 1.12 | 0.59 | 0.79 | 0.016 |
|  | 3 |  |  |  | 2.72 | 1.04 | 0.76 | 0.019 |
|  | 4 |  |  |  | 1.20 | 0.65 | 0.92 | 0.015 |
| 1 | 1 | 0.5 | 115° | 0.5 | 1.04 | 1.08 | 0.19 | 0.020 |
| 2 | 1 | 0.5 | 115° | 2 | 1.10 | 1.17 | 0.11 | 0.022 |
| 3 | 1 | 0.5 | 115° | 8 | 1.08 | 1.18 | 0.17 | 0.021 |
| 4 | 2 | 1.5 | 115° | 8 | 1.36 | 1.24 | 0.13 | 0.023 |
| 5 | 2 | 1.0 | 120° | 8 | 1.40 | 1.28 | 0.087 | 0.024 |
| 6 | 2 | 1.5 | 115° | 2 | 1.34 | 1.20 | 0.16 | 0.022 |
| 7 | 2 | 1.0 | 120° | 25 | 1.34 | 1.08 | 0.19 | 0.025 |
| 8 | 3 | 1.5 | 115° | 8 | 2.87 | 1.45 | 0.18 | 0.024 |
| 9 | 4 | 3.0 | 115° | 3 | 1.41 | 1.30 | 0.19 | 0.023 |
| Control | 4 | 3.0 | 115° |  | 1.37 | 1.27 | 0.26 | 0.022 |

Preparations A and B

To demonstrate the stability of stabilized chromium catalyst compositions used in the process of the invention solutions containing relatively high levels of chromium cations were prepared and observed under conditions typical of the decomposition process. A process stream resulting from air oxidation of cyclohexane was used as a solvent, chromium octoate as the catalyst and dodecylbenzenesulfonic acid as a stabilizer. The results are presented in Table 2. In preparation A approximately 70 ppm and in preparation B approximately 1000 ppm $Cr^{+3}$ were present. The S/Cr ratio for each was about 8. Each solution remained clear when cooled to ambient temperature. The results indicate that the chromium will remain in solution during the CHHP decomposition reaction and will not cause fouling.

TABLE 2

| Time (min) | Temp (°) A | B | Press (psig) A | B | Description A | B |
|---|---|---|---|---|---|---|
| 0 | 114 | 113 | 0 | 0 | clear, colorless | clear, green |
| 2 | 113 | 114 | 10 | 12 | clear, pale yellow-green | " |
| 4 | 113 | 115 | 20 | 20 | clear, pale yellow-green | " |
| 6 | 113 | 116 | 24 | 24 | clear, pale yellow-green | " |
| 8 | 113 | 117 | 26 | 28 | clear, pale yellow-green | " |
| 10 | 114 | 117 | 28 | 30 | clear, pale yellow-green | " |
| 12 | 114 | 117 | 30 | 30 | clear, pale yellow-green | " |
| 14 | 114 | 116 | 30 | 31 | clear, pale yellow-green | " |
| 16 | 114 | 116 | 30 | 31 | clear, pale yellow-green | " |
| 18 | 114 | 116 | 31 | 31 | clear, pale yellow-green | " |
| 20 | 114 | 116 | 31 | 31 | clear, pale yellow-green | " |

The invention being claimed is:

1. In a process for producing a mixture containing cyclohexanol and cyclohexanone wherein cyclohexane is oxidized to provide a reaction mixture containing cyclohexyl hydroperoxide and the cyclohexyl hydroperoxide is subsequently decomposed in the presence of starting cyclohexane to provide a mixture containing cyclohexanol and cyclohexanone, the improvement comprising conducting the decomposition step by contacting a reaction mixture containing cyclohexane and from about 0.1 to about 10% by weight of cyclohexyl hydroperoxide with a catalytic amount of a catalyst composition consisting essentially of (a) at least one cyclohexane-soluble salt of a transition metal selected from the group consisting of chromium, cobalt, iron, manganese, molybdenum and vanadium and having an anion selected from the group consisting of carboxylates, sulfonates, and alkylphosphates and (b) a sulfonate anion of a cyclohexane-soluble compound selected from the group consisting of alkyl and alkylarenesulfonic acids, alkylammonium sulfonates, alkylphosphonium sulfonates and mixtures thereof, at a temperature of from about 80° to 130° C., at a pressure of from 210–2410 kPa gauge, and at a mol ratio at sulfur to transition metal of from about 0.1 to about 100.

2. A process according to claim 1 wherein for component (b) of the catalyst composition the sulfonate anion is present as an alkylsulfonic acid, an alkylarenesulfonic acid or a mixture thereof, wherein each alkyl group in both components has from 8 to 22 carbon atoms.

3. A process according to claim 2 wherein the temperature is from about 110° to about 130° C.

4. A process according to claim 3 wherein the catalyst composition is present in an amount sufficient to provide from about 0.1 to about 100 ppm of metal by weight based on the total reaction mixture.

5. A process according to claim 4 wherein the catalyst composition is present in an amount sufficient to provide from about 0.1 to about 10 ppm of metal by weight based on the total reaction mixture.

6. A process according to claim 5 wherein the mol ratio of sulfur to transition metal is from about 1–10.

7. A process according to claim 6 wherein the catalyst composition is prepared prior to introduction into the reaction mixture, said introduction being effected immediately after said mixture leaves its oxidation stage or as said mixture enters its decomposition stage.

8. A process according to claim 7 wherein the sulfonic acid is an alkylarenesulfonic acid having an alkyl group of from 8–12 carbon atoms.

9. A process according to claim 8 wherein the alkylarenesulfonic acid is dodecylbenzenesulfonic acid or dinonylnaphthalenesulfonic acid.

10. A process according to claim 9 wherein the alkylarenesulfonic acid is dinonylnaphthalenesulfonic acid.

11. A process according to claim 10 wherein the transition metal is chromium or cobalt.

12. A process according to claim 11 wherein the transition metal is chromium.

* * * * *